United States Patent [19]

Maxwell

[11] 4,125,480

[45] Nov. 14, 1978

[54] PROCESS FOR REACTIVATING USED SILVER ETHYLENE OXIDE CATALYSTS

[75] Inventor: Ian E. Maxwell, Amsterdam, Netherlands

[73] Assignee: Shell Oil Company, Houston, Tex.

[21] Appl. No.: 843,199

[22] Filed: Oct. 18, 1977

[30] Foreign Application Priority Data

Oct. 21, 1976 [GB] United Kingdom .............. 43712/76

[51] Int. Cl.$^2$ .................. B01J 23/96; C07D 301/10; C07D 303/04
[52] U.S. Cl. .................................. 252/414; 252/412; 252/420; 260/348.34
[58] Field of Search ....................... 252/420, 412, 414; 260/348.34

[56] References Cited

U.S. PATENT DOCUMENTS

| | | | |
|---|---|---|---|
| 2,194,602 | 3/1940 | Law ................................ | 260/348.34 |
| 3,962,136 | 6/1976 | Nielson et al. ..................... | 252/454 |
| 4,007,135 | 2/1977 | Hayden et al. ................. | 260/348.34 |
| 4,010,115 | 3/1977 | Nielson et al. ..................... | 252/454 |
| 4,033,903 | 7/1977 | Maxwell ............................ | 252/476 |
| 4,066,575 | 1/1978 | Wihnick ............................ | 252/476 |

FOREIGN PATENT DOCUMENTS 2,519,599   7/1976   Fed. Rep. of Germany.

*Primary Examiner*—Winston A. Douglas
*Assistant Examiner*—P. E. Konopka

[57] ABSTRACT

The performance of used supported silver-based ethylene oxide catalysts is improved by a) washing the used catalyst with water or a mixture of water with a water-miscible organic solvent and b) depositing on the washed catalyst from about 0.00004 to about 0.008 gram equivalent weights per kilogram of total catalyst of ions of one or more of the alkali metals sodium, potassium, rubidium or cesium.

5 Claims, No Drawings

PROCESS FOR REACTIVATING USED SILVER ETHYLENE OXIDE CATALYSTS

BACKGROUND OF THE INVENTION

1. Field of the Invention

This invention relates to a process for reactivating used silver-based ethylene oxide catalysts by first washing the used catalyst and then depositing thereon alkali metal ions.

2. Description of the Prior Art

It is known that the activity of silver catalysts, and particularly their selectivity with respect to the formation of ethylene oxide often decreases during the use of these catalysts in the manufacture of ethylene oxide.

German patent specification No. 2,519,599 published July 1, 1976, discloses a process for the reactivation of used catalysts by impregnating the catalyst with an impregnating solution consisting of 0.1 to 5%w of water, 0.05 to 0.4% of cesium and/or rubidium nitrate, and an aliphatic alcohol having 1–3 carbon atoms, and subsequently evaporating the alcohol at a temperature of 70° to 120° C., optionally by purging with nitrogen, whereby 1 to 1000 ppm of cesium and/or rubidium are deposited on the catalyst.

U.S. Pat. No. 4,033,903 issued July 5, 1977, taught that the selectivity of used silver catalysts is improved by depositing from 0.00004 to 0.008 gram equivalent weights per kilogram (based on the entire catalyst) of ions of one or more of the alkali metals potassium, rubidium or cesium on the catalyst. This is done by impregnating the catalyst with a solution of one or more compounds, for example salts, or these alkali metals in a suitable solvent such as, for example, methanol, ethanol, isopropanol, acetone, methyl acetate or tetrahydrofuran.

However, the improvement of the selectivity obtained by the means taught by German Pat. No. 2,519,599 and U.S. Pat. No. 4,033,903 is not always as high as one would wish. This is particularly the case when the silver catalyst already contains alkali metals, such as for example the catalysts described in U.S. Pat. No. 3,962,136 issued June 8, 1976 and U.S. Pat. No. 4,010,115 issued Mar. 1, 1977 or when the catalyst is partially poisoned with contaminants, such as for example sulphur compounds.

It has now been found that in reactivating such catalysts superior results over the prior art is obtained when the used silver catalyst is first washed with water or a mixture of water with a water-miscible organic solvent before the alkali metals are deposited thereon. This is contrary to the teaching in German Patent Specification No. 2,519,599 for it is stated there that the presence of more than 10% by weight of water in the impregnating solution damages the catalyst. It also appears from Example 20 of the said German patent specification that a used, but still rather active silver catalyst is almost completely deactivated by treating it with an aqueous solution of cesium nitrate.

SUMMARY OF THE INVENTION

According to the present invention a process for improving the performance of silver catalysts which have been used in the preparation of ethylene oxide by reacting ethylene with molecular oxygen comprises (a) washing the used catalyst with water or a mixture of water with a water-miscible organic solvent, and (b) depositing from 0.00004 to 0.008 gram equivalent weights per kilogram (based on the entire catalyst) of ions of one or more of the alkali metals sodium, potassium, rubidium or cesium on the washed catalyst.

DESCRIPTION OF THE PREFERRED EMBODIMENTS

It has been found that when a used silver catalyst is washed with water or a mixture of water with a water-miscible organic solvent its selectivity decreases substantially. However, it has also been found that the activity and/or selectivity of the catalyst is raised by depositing sodium, potassium, rubidium and/or cesium on the washed catalyst. By this procedure catalysts which are more active and/or selective than the untreated used catalyst can be prepared. The mixture of water with the water-miscible organic solvent preferably contains at least 20% by weight, more preferably at least 50% by weight of water, but water itself is the most preferred washing agent. Examples of suitable organic solvents are methanol, ethanol, isopropanol, and acetone.

The wash is carried out in any conventional manner, for example by percolating the used silver catalyst with 1–10 times its volume of water, at room temperature. Alternatively, by way of example a volume of water of 0.5–10 times the catalyst volume may be recycled over the catalyst 2–10 times. After draining off the liquid, this procedure may be repeated by one or more times with fresh water. After the washing step the catalyst is preferably dried. This is done by heating the catalyst preferably at a temperature between 50° and 200° C. depending on the solvent to be removed. More preferably the catalyst is dried by purging it with a gas stream, for example nitrogen, air, hydrogen or methane, preferably at a temperature between 15° and 200° C. If desired, in order to reduce drying times, the drying step may be preceded by washing the catalyst with a low-boiling, water-miscible solvent, preferably having a boiling point below 100° C., for example methanol, ethanol, isopropanol or acetone.

The ions of sodium, potassium, rubidium and/or cesium is deposited on the washed catalyst by impregnating it with a solution of one or more compounds of these alkali metals in a suitable solvent, particularly an organic solvent. Examples of suitable compounds are the hydroxides, nitrates, chlorides, iodides, bromides, bicarbonates, and carbonates of sodium, potassium, rubidium or cesium or organic derivatives of these alkali metals, for example, their alkoxides, such as the isopropoxides, or their salts with organic carboxylic acids, such as, for example, the acetates, oxalates, tartrates and lactates. Suitable solvents are, for example, alkanols having 1 to 6 carbon atoms such as for example methanol, ethanol, and isopropanol, and acetone, methyl acetate and tetrahydrofuran. If desired, the solubility of the alkali metal compounds in the solvent may be increased by the use of complexing agents, such as, for example, macrocyclic polyethers of the type described in British Patent Specifications Nos. 1,108,921 and 1,285,367, or by the addition of water. The amount of water in the solvent is preferably below 20% by weight, most preferably below 10% by weight. Acetone is the preferred solvent. The amount of the impregnating solution and the concentration of the alkali metal therein should be sufficient to deposit between about 0.00004 and about 0.008, preferably between about 0.0001 and about 0.002 gram equivalent weights per kilogram of total catalyst of the alkali metal on the catalyst. If desired, the impregnating solution may be recirculated over the catalyst.

After the impregnation with the solution of alkali metal compound(s), the excess of solvent is removed. This is done at atmospheric, sub- or superatmospheric pressure. The catalyst is heated at a temperature, for example between about 50° and about 200° C., for a time between, for example, about 0.5 and about 48 hours, particularly between about 2 and about 16 hours depending on the solvent to be removed. During the drying treatment, a gas such as, for example, nitrogen, air, hydrogen, noble gases, carbon dioxide, methane or mixtures of these gases may be passed over the catalyst. Freeze drying or drying in vacuum at room temperature is also suitable.

If desired, the process of the invention is carried out in the reactor used for the manufacture of ethylene oxide. For example, water and the impregnating solution of one or more compounds of sodium, potassium, rubidium or cesium is successively passed through the reactor containing the used silver catalyst, and the intermediate and final drying steps are effected by heating the catalyst in a suitable gas stream.

The process of the invention not only improves the selectivity of the silver catalysts but often also their activity. This means that after reactivation the catalyst gives a higher conversion at the same reaction temperature than prior to the reactivation procedure, or alternatively, reaches the same conversion at a lower temperature. The use of lower reaction temperatures is of practical interest since the formation of undesirable side products, such as carbon dioxide, formaldehyde and/or acetaldehyde, increases at higher temperatures.

The reactivated silver catalysts according to the invention are used for the production of ethylene oxide by contacting ethylene in the vapor phase with a molecular oxygen-containing gas at a temperature of from about 150°–300° C., preferably about 190°–285° C., most preferably about 210° to about 275° C. in the presence of such a catalyst. The further conditions for carrying out such a process have been described in the prior art, for example the prior art mentioned in U.S. Pat. Nos. 3,962,136 and 4,010,115.

In a preferred application of the reactivated silver catalysts of the invention, ethylene oxide is produced by contacting an oxygen-containing gas (containing at least 95% oxygen) together with ethylene, a diluent gas and a moderator, with a catalyst according to the invention at a temperature in the range of from about 190° C. to about 285° C., and preferably about 210° C. to about 275° C.

The resulting ethylene oxide is separated and recovered from the reaction products by conventional methods.

The reactivation of silver catalysts according to the present invention as well as the use of thse catalysts in the production of ethylene oxide will be further described by the following Examples which are provided for illustration and are not to be construed as limiting the invention.

EXAMPLE I

A used potassium-containing silver catalyst of the type described in U.S. Pat. No. 4,010,115 (catalyst A) was tested for the production of ethylene oxide by charging it in a reactor tube with an internal diameter of 2 cm and a bed length of 20 cm. A gas mixture consisting of 25%m of ethylene, 8% of oxygen, 1.7 ppm of dichloroethane and the remainder nitrogen was passed over the catalyst at atmospheric pressure and a gaseous hourly space velocity of 250 $h^{-1}$.

The ethylene oxide selectivity attained at an oxygen conversion of 40%m, and the temperature required to attain that oxygen conversion is indicated in Table I.

The following catalysts, B, C and D were tested in an identical manner.

Catalyst B was prepared by soaking 100 g of catalyst A with 100 ml of a solution of 43.3 mg CsCl in acetone containing 5% by weight of water for at least 10 minutes. After draining off the excess solution, the catalyst was dried in an oven at 120° C. for 16 hours.

Catalyst C was prepared by washing 100 g of catalyst A twice for ½ hour with 200 ml of water while stirring at a temperature of 20° C., draining off the excess water, and then drying in air in an oven at 120° C. for 16 hours.

Catalyst D was prepared by soaking 100 g of catalyst C with 100 ml of a solution of 43.3 mg CsCl in acetone containing 5% by weight of water for at least 10 minutes. The catalyst was dried in the same way as catalyst B.

TABLE I

| Catalyst | Ethylene oxide selectivity, %m at 40%m oxygen conversion | Temperature, ° C |
|---|---|---|
| A | 70.3 | 268 |
| B | 74.0 | 281 |
| C | 59.1 | 265 |
| D | 75.6 | 258 |

From Table I it appears that catalyst D which was obtained by reactivating the spent catalyst (catalyst A) by means of the process according to the invention is more active and selective than catalyst A. Catalyst D is also more active and selective than catalyst B obtained by treating catalyst A with a cesium-containing solution without a preceding water wash. The low selectivity of catalyst C shows the unfavorable influence of just washing the catalyst with water.

EXAMPLE II

A spent potassium-containing silver catalyst of the type described in U.S. Pat. No. 4,010,115 (catalyst E) was tested for the production of ethylene oxide in a similar way as described in Example I.

The ethylene oxide selectivity attained at an oxygen conversion of 40%m, and the temperature required to attain that oxygen conversion is indicated in Table II.

The following catalysts F, G and H were tested in an identical manner.

Catalyst F was prepared by washing 200 g of catalyst E twice for 1 hour with 1000 ml of water at a temperature of 20° C., and then drying it by 120° C. for 16 hours.

Catalyst G was prepared by soaking 100 g of catalyst F with 100 ml of a solution of 20 mg NaCl in acetone containing 5% by weight of water for at least 10 minutes. The catalyst was dried in the same way as catalyst F.

Catalyst H was prepared by soaking 100 g of catalyst F with 100 ml of a solution of 20 mg KCl in acetone containing 5% by weight of water for at least 10 minutes. The catalyst was dried in the same way as catalyst F.

TABLE II

| Catalyst | Ethylene oxide selectivity, %m at 40%m oxygen conversion | Temperature °C |
| --- | --- | --- |
| E | 72.5 | 267 |
| F | 61 | 267 |
| G | 71.4 | 262 |
| H | 72.5 | 261 |

EXAMPLE III

A used potassium-containing silver catalyst of the type described in U.S. Pat. No. 4,010,115 (catalyst I) was tested for the production of ethylene oxide by charging it in a reactor tube with an internal diameter of 2 cm and a bed length of 20 cm. A gas mixture consisting of 30%m of ethylene, 7.5%m of oxygen, 7 ppm of vinyl chloride and the remainder nitrogen was passed over the catalyst at atmospheric pressure and a gas hourly space velocity of 240 $h^{-1}$.

The ethylene oxide selectivity attained at an oxygen conversion of 40%m, and the temperature required to attain that oxygen conversion are indicated in Table III.

The following catalysts J and K were tested in a similar manner. Catalyst J was prepared by washing 100 grams of catalyst I four times for 1 hour with 200 ml of distilled water while stirring at a temperature of 20° C., draining off the excess of water, and then stirring the catalyst with 200 mls of acetone for ½ hour. After draining off the excess of acetone the catalyst was dried in air in an oven at 120° C. for 16 hours.

Catalyst K was prepared by impregnating 100 g of catalyst J with 200 mls of a solution of 50 mg CsCl in acetone containing 5% by weight of water. The impregnation was carried out by percolating the solution over the catalyst over a period of 15 minutes and collecting the effluent solution. This procedure was repeated four more times by percolating the effluent solution over the catalyst after which the impregnating solution was drained off and the catalyst dried in an oven at 120° C. for 16 hours.

TABLE III

| Catalyst | Ethylene oxide selectivity, %m at 40%m oxygen conversion | Temperature °C |
| --- | --- | --- |
| I | 72.2 | 260 |
| J | 69.3 | 256 |
| K | 77.8 | 259 |

What is claimed is:

1. A process for improving the performance of used silver-based catalysts used for the production of ethylene oxide by contacting ethylene in the vapor phase with a molecular oxygen-containing gas at a temperature of from about 150°-300° C. which comprises:
    (a) washing the used catalyst with 1-10 times its volume of water or a mixture of at least ten percent water with a water-miscible organic solvent, and
    (b) depositing on the washed catalyst from about 0.00004 to about 0.008 gram equivalent weights per kilogram of total catalyst of alkali metal ions selected from the group consisting of sodium, potassium, rubidium, cesium, or mixtures thereof by impregnating the catalyst with a solution of alkali metal ions dissolved in a solvent selected from the group consisting of alkanols having 1 to 6 carbon atoms, acetone methyl acetate and tetrahydrofuran.

2. The process of claim 1 wherein the water-miscible organic solvent is selected from the group consisting of methanol, ethanol, isopropanol, acetone and mixtures thereof.

3. The process of claim 1 wherein the solvent is an alkanol having 1 to 6 carbon atoms.

4. The process of claim 1 wherein the solvent is acetone.

5. The process of claim 1 wherein the amount of alkali metal deposited on the washed catalyst is between about 0.0001 and about 0.002 gram equivalent weights per kilo of total catalyst.

* * * * *